(12) United States Patent
Storm

(10) Patent No.: US 8,082,606 B2
(45) Date of Patent: Dec. 27, 2011

(54) WASTE RECEIVING DEVICE FOR INCONTINENT PERSONS

(76) Inventor: David B. Storm, Cookeville, TN (US)

(*) Notice: Subject to any disclaimer, the term of this patent is extended or adjusted under 35 U.S.C. 154(b) by 156 days.

(21) Appl. No.: 12/427,158

(22) Filed: Apr. 21, 2009

(65) Prior Publication Data

US 2009/0260143 A1  Oct. 22, 2009

Related U.S. Application Data

(60) Provisional application No. 61/046,988, filed on Apr. 22, 2008.

(51) Int. Cl.
*E03D 9/10* (2006.01)
(52) U.S. Cl. .................................. 4/319; 4/480
(58) Field of Classification Search .............. 4/319, 320, 4/449, 480, 483, 317, 318; 241/46.08
See application file for complete search history.

(56) References Cited

U.S. PATENT DOCUMENTS

| | | | | |
|---|---|---|---|---|
| 1,996,325 A * | 4/1935 | Cox | ................................. | 4/111.1 |
| 2,779,948 A * | 2/1957 | Houle | ................................. | 4/319 |
| 3,439,361 A * | 4/1969 | Moore | ............................... | 4/319 |
| 3,564,619 A * | 2/1971 | Magathan | ......................... | 4/319 |
| 4,170,798 A * | 10/1979 | Krumdieck | ....................... | 4/319 |
| 4,285,719 A * | 8/1981 | Criss | ................................... | 71/13 |
| 5,170,516 A * | 12/1992 | Davison | ........................... | 4/484 |
| 6,442,771 B1 * | 9/2002 | Meier | ................................ | 4/319 |
| 6,721,965 B1 * | 4/2004 | Alston | .......................... | 4/256.1 |
| 7,309,072 B2 | 12/2007 | Storm | | |
| 2009/0019631 A1 * | 1/2009 | Ruttler | .............................. | 4/480 |
| 2009/0077731 A1 * | 3/2009 | Hiranuma et al. | ................ | 4/319 |
| 2009/0165196 A1 * | 7/2009 | Mochizuki et al. | ............... | 4/315 |

* cited by examiner

*Primary Examiner* — Gregory Huson
*Assistant Examiner* — Janie Christiansen
(74) *Attorney, Agent, or Firm* — Knox Patents; Thomas A. Kulaga

(57) ABSTRACT

A waste receiving device for disposing of fecal waste from an incontinent person being bathed. The waste receiving device includes a receiver and a waste processing mechanism that discharges processed waste to a waste water drain. The waste processing mechanism includes a strainer and/or a masticator for processing the fecal waste such that the processed waste has a maximum solids size that is suitable for passing through the waste water drain. The strainer is a filter with one or more openings that are sized to pass only waste that is not larger than the maximum solids size. The strainer, in one embodiment, is incorporated in a removable basket. The masticator, in various embodiments, is a manually operated mechanical reducer or a powered reducer, such as one operated by pressurized water.

19 Claims, 6 Drawing Sheets

WASTE RECEIVING DEVICE FOR INCONTINENT PERSONS

CROSS-REFERENCE TO RELATED APPLICATIONS

This application claims the benefit of U.S. Provisional Application No. 61/046,988, filed Apr. 22, 2008.

STATEMENT REGARDING FEDERALLY SPONSORED RESEARCH OR DEVELOPMENT

Not Applicable

BACKGROUND OF THE INVENTION

1. Field of Invention

This invention pertains to a waste receiving device for incontinent persons. More particularly, this invention pertains to a waste receiving device that receives waste as it is produced by an incontinent person being bathed in flowing water and passes all of the waste received that is capable of flowing through an associated drain.

2. Description of the Related Art

Elder care facilities often provide hygienic care for its residents. Daily bathing in warm flowing water is both a hygienic and relaxing activity. It is not uncommon for persons to be wheeled into a bathing area while the person is seated on a bath chair. The bath chair is typically a wheeled chair that allows water to flow through it so as to prevent accumulation or collection of bath water on the chair. The bath chair also commonly includes a seat portion that has an opening, such as is found on a toilet seat. The person seated on the bath chair is wheeled adjacent a shower or other source of bathing water where the person is bathed.

Incontinent accidents commonly occur when persons are bathed in warm flowing water because of the relaxation of the body. Because the bathing areas are shared by multiple persons, it is not unusual for one person to come into contact with the waste of another person. Also, because the bath chair has wheels and is used to transport the person, the wheels often pass through the bodily waste and track that waste on the floor as the person is transported from the bathing area.

*Clostridium difficile* (*C. Difficile*) is a deadly bacteria. It is the most serious cause of antibiotic-associated diarrhea (AAD) and can lead to pseudomembranous colitis, a severe infection of the colon. The *C. difficile* bacteria naturally reside in the body at non-toxic levels, normally. Transmission of *C. difficile* from one person to another often follows the vector from fecal matter to oral ingestion, such as can occur when fecal matter contaminates an object that is then touched by someone. The person has contaminated hands, which handles food and/or medicine, which causes the contamination to be ingested, thereby infecting the person. The infected person may experience overgrowth of *C. difficile*. The overgrowth is harmful because the bacterium releases toxins that potentially causes bloating, constipation, and diarrhea with abdominal pain, which may become severe. In elderly persons or those with frail immune systems, overgrowth of *C. difficile* often has severe, and sometimes deadly, consequences.

Elder care providers do not have an adequate way to maintain contaminant-free surroundings when such incontinent accidents occur. Such accidents often occur in common bath areas where other persons may come into contact with the fecal waste. If such accidents occur in private areas, but the person is transported on a wheeled device, the wheels are a common transport mechanism for the *C. difficile*. A common waste pan positioned to capture waste is not useful because the flowing water will cause the pan to overflow during the bathing process.

Another example of a device that does not dispose of the waste as it is captured is a water caddy configured to fit under the seat of a person in a shower apparatus. U.S. Pat. No. 7,309,072, issued on Dec. 18, 2007, to David B. Storm discloses a fluid container for capturing, containing, transporting, and emptying a fluid. The water caddy is configured to transport the waste to another location where it can be disposed, such as in a toilet, which has a drain sized to accommodate fecal matter.

BRIEF SUMMARY OF THE INVENTION

A waste receiving device for preventing fecal waste from contaminating the environment is disclosed. The waste receiving device includes a receiver, a strainer and/or a masticator, and a conduit to a drain that has a size smaller than normally used to dispose of fecal matter. In this way, fecal matter from an incontinent person is contained and/or directed to a floor drain to avoid contamination of the surrounding area. The waste receiving device is sized to fit under a bath chair or, with a seat, to be used as a support for the person.

In one embodiment, the receiver includes a seat proximate its upper opening. The seat is configured for a person to sit upon. In another embodiment, the receiver includes a notch or depressed portion in the lip. The receiver is configured to be positioned under a bath chair with a toilet type seat. The notch is configured to allow clearance for any portion of the person's body that protrudes though the seat opening when the bath chair is moved relative to the waste receiving device. The notch prevents the body parts from being pinched between the seat of the bath chair and the receiver.

In one embodiment, the waste receiving device includes a strainer positioned inside the receiver. The strainer has a plurality of openings that are sized to only pass objects that will fit through a drain positioned under the waste receiving device. In one such embodiment, the strainer is removable after use in order to allow for the disposal of any fecal matter captured by the strainer.

In one embodiment, the waste receiving device includes a masticator that receives fecal matter from the receiver and discharges a slurry of water and fecal matter with a consistency suitable for discharging into a drain. The masticator, sometimes called a macerator, is a device that reduces the size of fecal matter, such as by grinding, shredding, or otherwise softening or breaking apart the fecal matter. In various embodiments, the masticator is operated manually or by electrical, hydraulic, or pneumatic power.

In one embodiment, the receiver is supported by a shroud. The shroud extends from the receiver to the floor and provides a stable support for the receiver. In one embodiment, the shroud is attached or secured to the floor over a drain. The lip of the shroud adjacent the floor includes passages or openings that allow the free passage of water so that water in the environment flows into the drain. The passages are sized and configured to prevent objects from approaching the drain if those objects have a size that could potentially clog the drain.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

A waste receiving device 100 for use when bathing a person who is potentially incontinent is disclosed. The waste receiving device 100 prevents contamination of the environment during the bathing of a person who is potentially incontinent.

Figure 1:
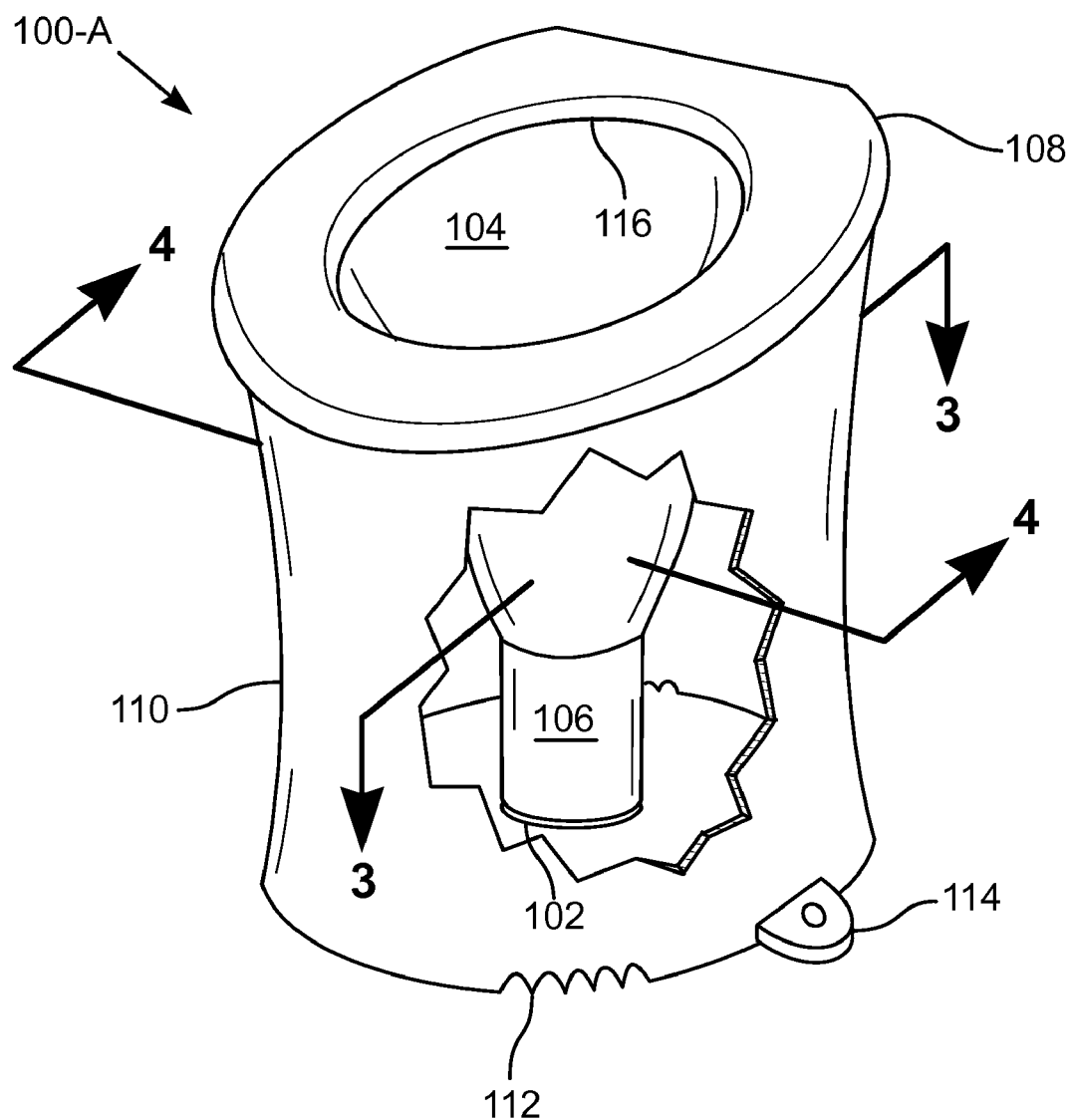
FIG. 1 is a perspective view of one embodiment of a waste receiving device with a partial cut-away.

FIG. 1 illustrates a perspective view of one embodiment of a waste receiving device 100-A with a partial cut-away of the shroud 110. In the illustrated embodiment, the waste receiving device 100-A includes a bowl, or receiver, 104 and a conduit 106. The receiver 104 has a wide orifice at its upper end with rounded and/or angled walls tapering down to the conduit 106. A seat 108 is attached to the receiver 104 above the wide orifice. The seat 108 has a centrally located opening 116. The seat 108 is sized for a person to sit upon it. In another embodiment, the upper end of the receiver 104 is the uppermost part of the receiving device 100-A and a seat 108 is not used.

The lower end of the receiver 104 communicates with the conduit 106, which is smaller than the orifice at the top of the receiver 104. The conduit 106 extends from the lower end of the receiver 104 to a floor drain 102. The conduit 106 is sized to direct waste into the floor drain 102 without the waste contacting the floor. In one embodiment, the conduit 106 fits into the floor drain 102. In another embodiment, the conduit 106 is located above the floor drain 102.

The receiver 104 and the conduit 106 have surfaces that release waste allowing the flow of water and pull of gravity to move the waste through to the floor drain 102. The waste that will not flow through the floor drain 102 will not be passed to the floor drain 102. Accordingly, such waste will not contaminate the floor or prevent the flow of other waste through the floor drain 102.

The height of the receiver 104 varies according to the application. For example, in a shower room, the height of the receiver 104 is such that a bathing chair fits over the waste receiving device 100-A. Also, where the receiver 104 includes the seat 108, the height of the receiver 104 is set at a comfortable seating height.

The conduit 106 and at least a portion of the bowl, or receiver, 104 is surrounded by a shroud 110. The shroud 110 is a support structure for the receiver 104. In the illustrated embodiment, the shroud 110 is attached to the top of the receiver 104 and extends downward adjacent the floor. In this way, the shroud 110 also surrounds the receiver 104. In other embodiments, the shroud 110 is attached to a lower surface of the receiver 104.

The bottom of the shroud 110 substantially matches the contour of the floor. Where the shroud 110 surrounds the floor drain 102, the bath water flowing around the outside of the receiving device 100 reaches the floor drain 102 by passing through grooves, or passages or openings, 112 along the bottom of the shroud 110. The grooves 112 are sized to prevent objects from reaching the floor drain 102 that will tend to block the floor drain 102. In other embodiments, the bottom of the shroud 110 and the floor surface define a gap that allows passage of water from the environment, such as is found in a shower or bathing area.

The illustrated shroud 110 includes one or more mounts 114. The mounts 114 secure the shroud 110 to the floor so that the incontinent person can sit comfortably on the seat 108 without substantial movement or instability. The size and number of mounts 114 vary according to the application. For example, where the receiving device 100 is being used with a bathing chair, the mounts 114 do not have to withstand the shifting weight of the person being bathed, so the mounts 114 do not require the structural strength required if someone were sitting on the seat 108.

Figure 2:
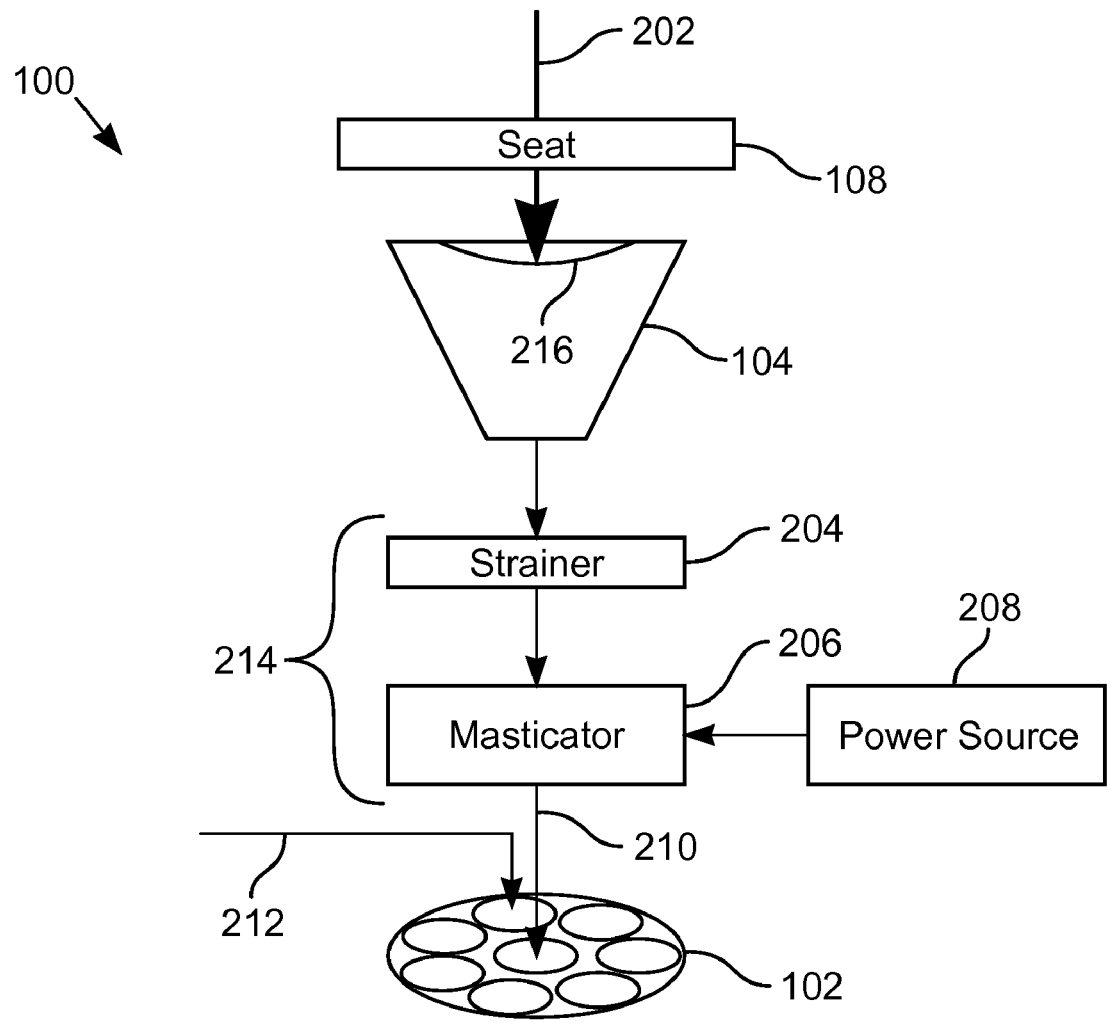
FIG. 2 is a schematic of one embodiment of a waste receiving device.

FIG. 2 illustrates a schematic of one embodiment of a waste receiving device 100. A seat 108 is positioned adjacent the upper end of a receiver 104. The fecal matter 202 enters the receiver 104 after which the fecal matter 202 encounters a waste processing mechanism 214. The outlet of the waste processing mechanism 214 passes waste water 210 into the drain 102. Environmental water 212 also enters the drain 102, such as through the passages 112 in the shroud 110.

The waste processing mechanism 214 receives fecal matter 202 from the receiver 104 and outputs waste water, or processed waste, 210. The processed waste 210 has a consistency and maximum particle/solids size suitable for passing through the drain 102. In other words, the fecal matter 202 is reduced by the waste processing mechanism 214 such that the processed waste 210 does not contain any fecal matter that has a size that is too large to pass through the drain 102.

The waste receiving device 100 has a height and is configured to be positioned beneath the posterior of a person, such as someone sitting in a bath chair or sitting on the seat 108 above the receiver 104. A commode apparatus is a device that a person sits or reclines upon that includes a provision for the person to pass waste such as fecal matter 202. For example, a bath chair with a potty seat is a commode apparatus. Likewise, a shower commode chair is a commode apparatus. If the person is supported on a commode apparatus, the seat 108 is not used but the upper opening of the receiver 104 is positioned beneath the opening in the support device. When the person is being bathed, bath water and any bowel movement falls into the receiver 104.

The receiver 104 has a bowl shape configuration to receive fecal matter 202 from a person positioned above the receiver 104. That is, the receiver 104 has a truncated conical shape with an opening at the top that has a larger area than the opening at the bottom. The inside of the receiver 104 has a surface that is conducive to allowing waste 202 to move through the receiver 104 without unduly sticking to the surface.

The receiver 104 includes a notch or depression 216 in the lip on top of the receiver 104 that is configured to prevent pinching of any body parts that may protrude into the receiver 104. For example, if a male is sitting in a bath chair with a potty seat, the male's scrotum and penis may hang through the potty seat and protrude below the bottom of the seat. When the bath chair is moved relative to the waste receiving device 100, the notch 216 allows the dangling body parts to pass over the lip of the receiver 104 without being pinched between the potty seat and the top lip of the receiver 104. The notch 104 is positioned on the side of the receiver 104 that faces the person support device when the device is positioned to be moved over the waste receiving device 100. The notch 216 allows the receiver 104 to extend upward with minimal clearance under the person support device, thereby ensuring that all fecal waste 202 is captured by the receiver 104 without creating a pinching hazard for the person. In another embodiment, the receiver 104 has a height that provides for sufficient clearance between the top of the receiver 104 and the bottom of the person support device's seat such that there is no pinching hazard.

In various embodiments, the waste processing mechanism 214 includes a strainer 204 and/or a masticator 206 and power source 208. The waste processing mechanism 214 functions to prevent the fecal matter 202 from contaminating the environment external to the waste receiving device 100. The mechanism 214 also functions to pass only processed waste 210 that is disposable through the drain 102. The drain 102 is a waste water drain. A waste water drain typically has an approximately 1½ inch diameter throat, such as a floor drain that is located in a shower area. The waste water drain is intended to receive only water and is neither intended nor configured to receive raw fecal matter. Raw fecal matter includes the feces excreted from a human before any processing and has, typically, a solid or semi-solid consistency. The drain 102 is not intended nor sized for disposing raw fecal matter. The processed waste 210 does not contain solids that are over a maximum solids size that is suitable for passing through a waste water drain 102. That is, the processed waste 210 has a maximum solids size that is less than or equal to the maximum size of solids that the drain 102 is able to receive and pass.

The strainer 204 prevents passage of fecal matter 202 solids that exceed a specified size. In one such embodiment the strainer 104 includes a barrier having openings of a size selected to block passage of any fecal matter 202 that will not pass through the drain 102. In various embodiments, the strainer 104 includes a basket and/or a fixed plate adjacent the bottom of or positioned below the receiver 104.

The masticator 206 and its power source 208 reduces the size and consistency of the fecal matter 202 such that the treated fecal matter, or processed waste, 210 is able to pass through the drain 102. In one embodiment, the masticator 206 is a mechanical device that grinds the fecal matter 202 with a power source 208 that is manually operated, such as a lever that is operated by pushing down with a foot. In another embodiment, the masticator 206 is a device that is powered by an electrical power source 208, such as a masticator 206 that is motor driven. In yet another embodiment, the masticator 206 is hydraulically or pneumatically operated with a fluid power source 208, such as a device with water jets that shred and eject waste with a slurry-type consistency.

In another embodiment, a strainer 204 is positioned before said masticator 204. The strainer 204 filters fecal matter 202 and prevents fecal matter solids above a specified size from entering the masticator 204, thereby allowing the masticator 206 to be sized to accommodate smaller sized fecal matter solids.

Figure 3:
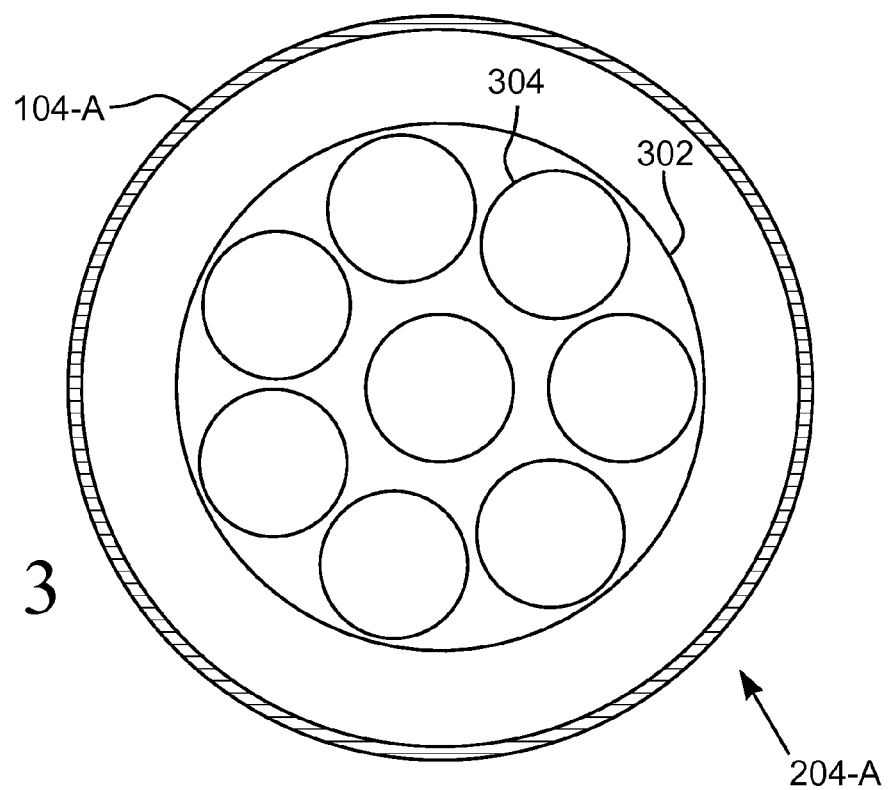
FIG. 3 is a cross-sectional top view of one embodiment of a strainer.

FIG. 3 illustrates a top view of one embodiment of a strainer 204-A in the flow path of the waste 202 from the receiver 104-A to the drain 102. The strainer 204-A includes a plate 302 with apertures 304. The plate 302 is secured in the receiver 104-A such that the plate 302 supports any fecal matter 202 that is retained by the plate 302. After the plate 302 captures and retains any fecal matter 202, the waste 202 is readily removed from the upper surface of the plate 302. The strainer 204-A is configured to retain the waste that will not flow through the drain 102 to avoid contaminating the floor or preventing the flow of other waste through the drain 102. In the illustrated embodiment, the strainer 204-A is located at the transition from the lower end of the receiver 104 to the conduit 106 to provide access to the waste retained by the strainer 204-A.

The apertures 304 are dimensioned to pass only waste 202 that is of a size that flows through the drain 102. That is, the apertures 304 have a diameter that is equal to the maximum solids size that is suitable for passing through a waste water drain 102.

The apertures 302 in the strainer 204-A are arranged to maximize the area available for the waste to flow through the strainer 204-A, while still preventing waste that will not pass through the drain 102 from passing through the strainer 204-A. The number of apertures 302 is sufficiently great to prevent the strainer 204-A from clogging or fouling from the waste that cannot flow through the strainer 204-A. The strainer 204-A is formed of a material that is not susceptible to corrosion or fouling by the waste flowing through the receiving device 100. The strainer 204-A is also sufficiently sturdy to support any waste captured and retained by the strainer 204-A.

Figure 4:
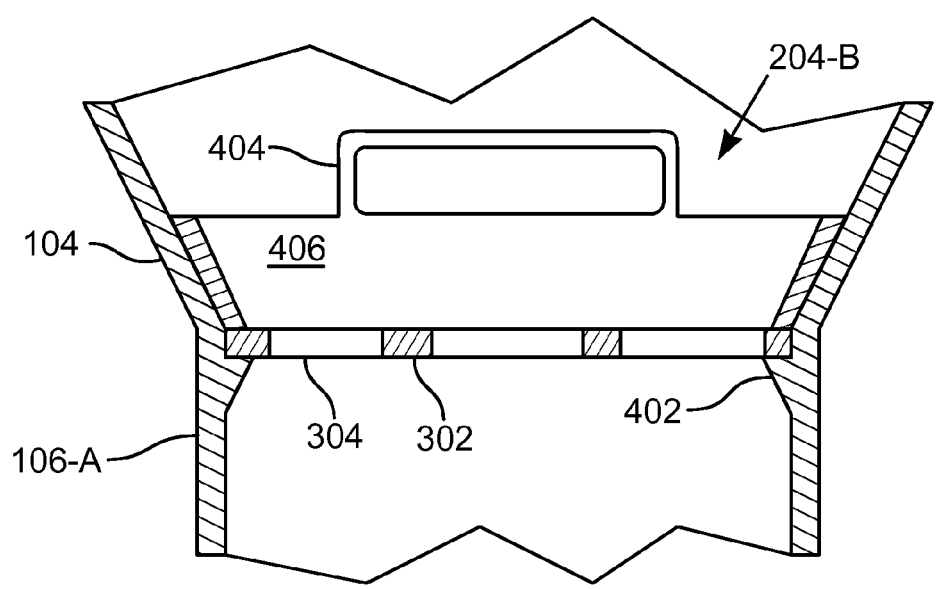
FIG. 4 is a cross-sectional side view of one embodiment of a strainer incorporated in a basket.

FIG. 4 illustrates a cross-sectional side view of another embodiment of a strainer 204-B configured as a basket. The strainer 204-B is releasably supported adjacent the connection of the receiver 104-B and conduit 106-B. The strainer 204-B is removably accessible from inside the receiver 104-B. The strainer 204-B provides for removing the waste 202 that does not pass through the strainer 204-B. Waste retained in the strainer 204-B is removed from the receiver 104-B and disposed by emptying the strainer 204-B into a waste receptacle.

The basket 204-B includes a plate 302 with a wall 306 that encircles the plate 302. The height of the wall 306 extending from the strainer 204-B is such that the strainer 204-B will capture and contain any waste that will not pass through the drain 102. The plate 302 includes apertures 304 that are sized to allow passage of waste 202 that does not exceed a specified size. The wall 306 of the illustrated strainer 204-B is shaped to fit the inside surface of the receiver 104-B.

Protruding upwards from the wall 306 is one or more handles 404 for removing the basket 204-B from the receiver 104-B. In one embodiment, the handles 304 are positioned at opposite sides of the wall 306 such that the basket 204-B is removable by lifting on the handles 304 and the person removing the basket 204-B will not have to come in contact with any retained waste. In one embodiment, the handles 404 are configured to engage a hook or other implement that a person uses to lift the basket 204-B out of the receiver 104 for disposal of the collected waste.

The strainer 204-B engages a ledge 402 that protrudes from the inside surface of the conduit 106-B. The ledge 402 supports the basket 204-B and serves to retain the basket 204-B in the receiver 104-B.

Figure 5:
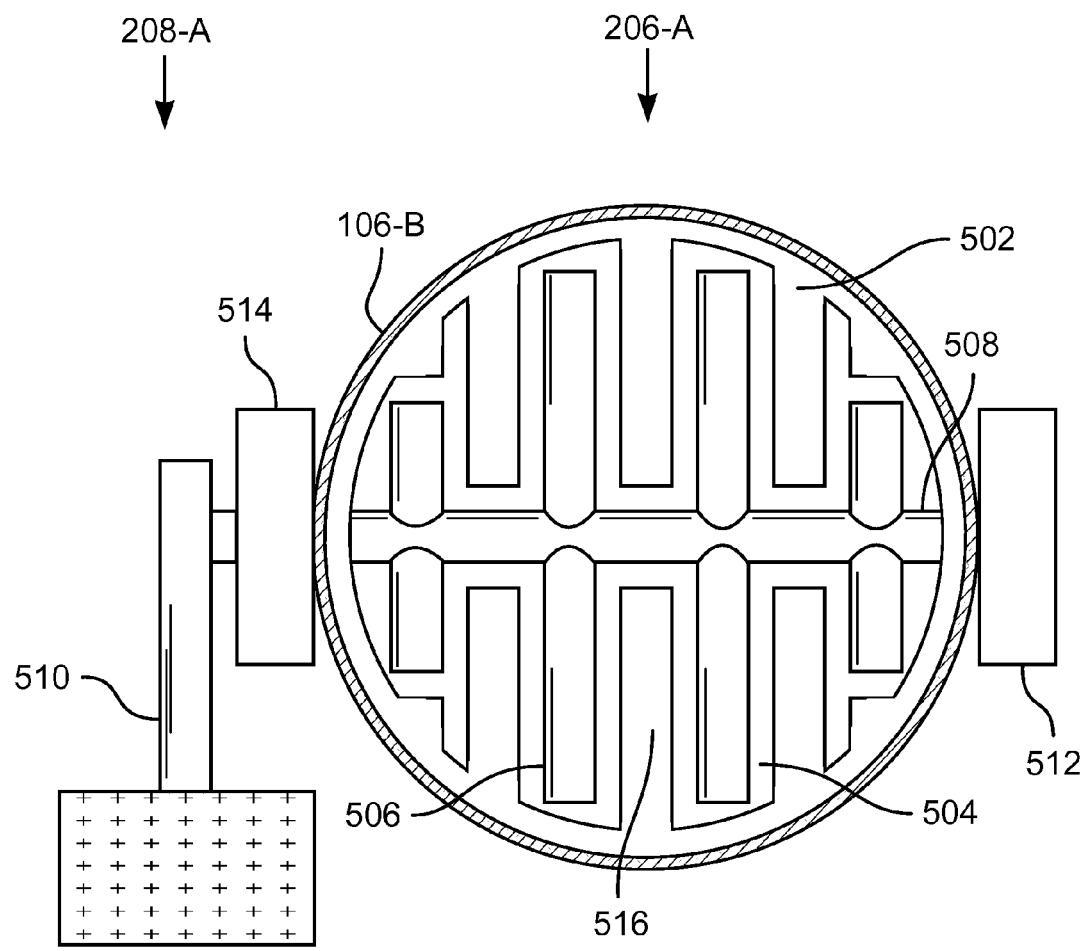
FIG. 5 is a top view of one embodiment of a grinder.
Figure 6:
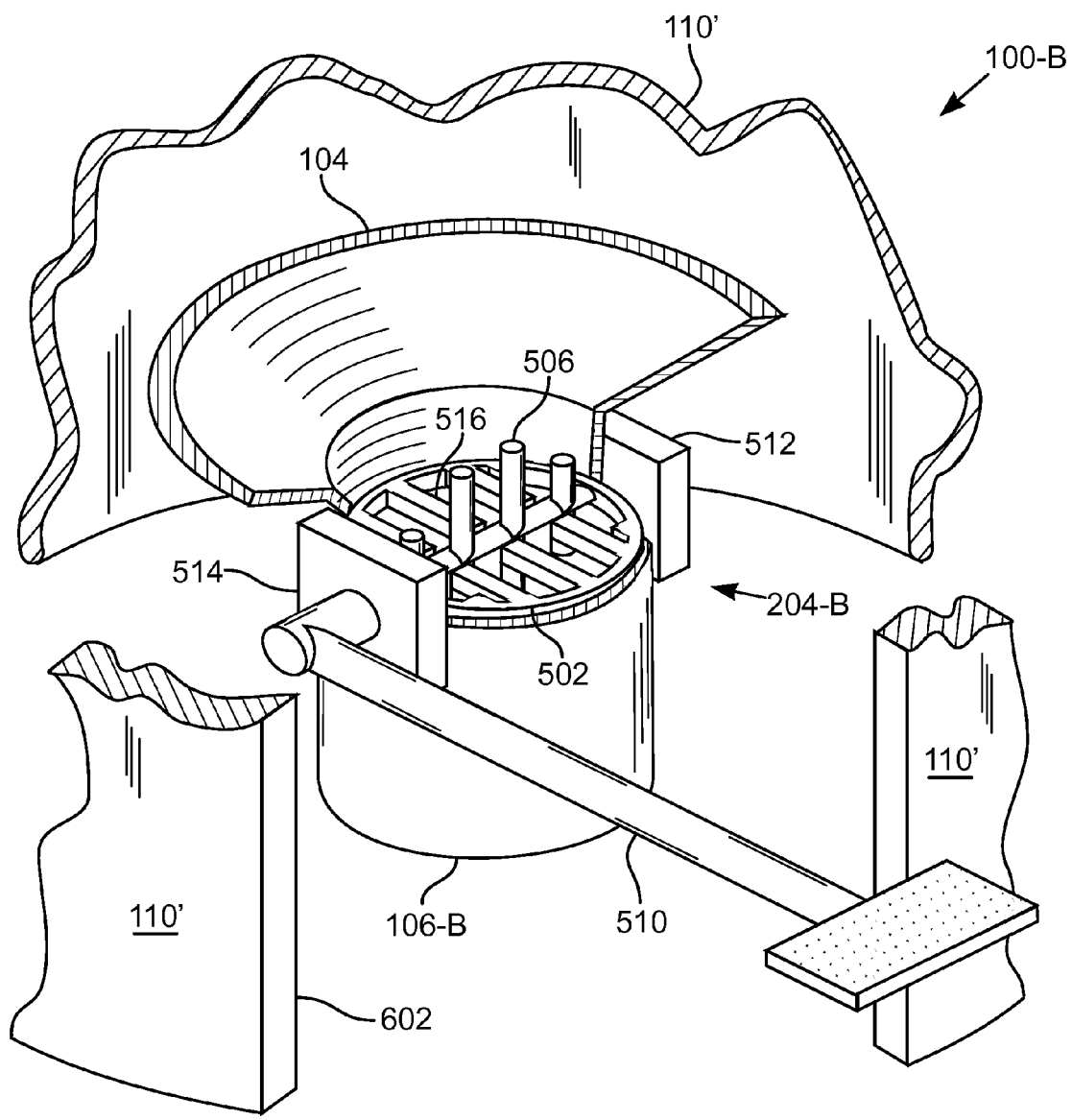
FIG. 6 is a partial perspective view of another embodiment of a waste receiving device with a grinder.

FIG. 5 illustrates a top view of one embodiment of a masticator, or grinder, 206-A. FIG. 6 illustrates a partial perspective view of another embodiment of a receiving device 100-B with a grinder 206-A. In the illustrated embodiment of the waste receiving device 100-B, the flow path of the waste 202 from the receiver 104 to the drain 102 includes a mechanical reducer that processes the waste that would not flow through the drain 102 so that the waste 202 will flow through the drain 102.

One such mechanical reducer is the illustrated grinder 206-A. The grinder 206-A includes an inlet that receives waste from the receiver 104. The grinder 206-A mechanically reduces the waste 202 such that the waste 202 flows through a drain 102. In various embodiments, the grinder 206-A is powered by a source 208 that is actuated by manual manipulation or switched on automatically when the presence of waste is detected. The grinder 206-A includes an outlet that passes the masticated waste through the conduit 106-B to the drain 102.

In the illustrated embodiment, the grinder 206-A is located within the conduit 106-B. In another embodiment, the grinder 206-A is incorporated in the receiver 104. In one embodiment, the grinder 206-A is positioned below a flexible shield, which discourages placing ones hands near the grinder 206-A. For waste that will not flow through the drain 102, the grinder 206-A masticates the waste so that the waste 202 is of a size and consistency that is capable of flowing through the drain 102.

In the illustrated embodiment, the grinder 206-A includes a plate 502, a shaft 508 with fingers 506, a spring assembly 512, and a pedal 510 connected to the shaft 508 through a gear box 514. The plate 502 has a cylindrical outer surface that fits within the conduit 106-B. Extending inward from the cylindrical portion of the plate 502 are multiple projections 516 that are spaced apart and parallel. The plate 502 receives the shaft 508, which rotates about an axis perpendicular to the axis of the cylindrical portion of the plate 502 and between the ends of the projections 516. The plate 502 includes an opening 504. The opening 504 is a series of parallel slots defined by the projections 516. The opening 504 is configured to receive the shaft 508 and the fingers 506, with the fingers 506 fitting between the projections 516. Further, the opening 504 is dimensioned and configured such that only waste that will pass through the drain 102 will pass through the opening 504.

Each of the fingers 506 is attached at one end to the shaft 508. The fingers 506 are spaced apart on the shaft 508, thereby forming a coplanar row of fingers 506. A single row of fingers 508 is repeated at 180 degrees around the shaft 508. The lengths of the fingers 506 vary such that when spaced apart on the shaft 508, which passes through the plate 502, the fingers 506 are able to pass through the opening 504 within the bounds of the plate 502. While the illustrated embodiment shows eight fingers 506, those skilled in the art will recognize that the number and configuration of the fingers 506 can be varied without departing from the spirit and scope of the present invention.

In the illustrated embodiment, the power source 208-B is a manually operated foot pedal assembly that includes a pedal 510 connected to a gear box 514, which is connected to a shaft 508 and a spring assembly 512. The shaft 508 is connected on one end to a spring assembly 512 and at the other end to a gear box 514. The gear box 514 is connected to a pedal 510. Movement of the pedal 510 operates the gear box 514 and causes the shaft 508 to rotate with a reciprocal movement. When the shaft 508 is rotated, the fingers 506 pass through the opening 504 with a corresponding motion. The spring assembly 512 returns the shaft 508, and the pedal 510, to a start position with the longitudinal axis of the fingers 506 perpendicular to the plane of the projections 516. In one embodiment, the spring assembly 512 includes a spiral spring of sufficient strength to return the shaft 508 and the pedal 510 to the start position. In other embodiments, the shaft 508 and the pedal 510 are returned to the start position by a helical or coil spring.

The grinder 206-A is within the flow path to the drain 102. Waste water flows through the opening 504 as will any fecal matter 202 that will also flow through the drain 102. Any waste that cannot flow through the drain is stopped by the projections 506. Pressing down on the pedal 510, such as with a person's foot, causes the shaft 508 to rotate and the fingers 506 to engage the projections 516. Any waste that is captured by the projections 506 will be caught between the fingers 506 and the projections 516 as the shaft 508 rotates. Any waste, such as fecal matter, that is too large to readily pass through the grinder 206-A is masticated by the fingers 506 engaging the projections 516. The mastication reduces the waste so that the waste passes through the drain 102. The illustrated embodiment of the finger 506 is cylindrical, that is, it has a circular cross section, other cross sections are possible, including a cross section that is square or oval or is a non-regular shape, as well as cross sections that vary in shape along the length of the finger 506.

In the illustrated embodiment, a shroud 110' provides access to the pedal 510 through a window, or opening 602. The opening 602 is sized to allow movement of the pedal 510 over its range of motion. The opening 602 is also not so large as to present a safety hazard. In another embodiment, a shaft between the pedal 510 and the grinder shaft 508 extends through a small hole in the shroud 110. In other embodiments, the shaft 508 rotates by a power source 208 that is driven by electric, pneumatic, or hydraulic power.

In other embodiments, the grinder 206-A includes a grinding mechanism that rotates about an axis parallel to the flow of waste. In one such embodiment, the grinder 206-A includes a rod, a blade, a strainer, a nut, and a housing. The rod is an elongated cylinder. The longitudinal axis of the rod is parallel to the flow of waste through the conduit. The blade is a thin sheet with a rectangular shape. The blade includes two cutting sides and a central opening. The two cutting sides are parallel to the longitudinal axis of the blade. The cutting sides are each tapered to a sharp edge. The central opening is located at the intersection of the midpoints of the longitudinal and lateral axes.

The strainer passes only the waste that will flow through the drain 102. The strainer has a central aperture sized to fit over the rod. The rod includes a strainer shoulder, two ends, a first end and a second end, and a blade shoulder. The strainer shoulder mates with the strainer locating the strainer vertically. The first end of the rod is threaded. The first end of the rod is dimensioned and configured to receive the central opening of the blade such that the blade does not rotate about the rod. The blade shoulder locates the blade vertically relative to the strainer. The nut fixes the blade to the first end of the rod.

The housing includes a sealed opening and a waste passage. The housing receives a shaft of an electric motor through the sealed opening. The electric motor is operably connected to the second end of the rod. The rod and the blade are centrally located within the housing. The housing is attached to the conduit such that the flow of waste passes through the housing to the outlet. While the described embodiment connects the blade to the rod using a nut and threaded end, those skilled in the art will recognize that other fastening means can be used without departing from the spirit and scope of the present invention.

The electric motor turns the blade. The blade reconfigures the waste such that it will pass through the strainer and corresponding drain by rotating about the rod. The motor is operated by a power source that is controlled by a switch. In various embodiments, the switch is operated by a photoelectric sensor, a foot switch, a wall switch, or other switch.

Figure 7:
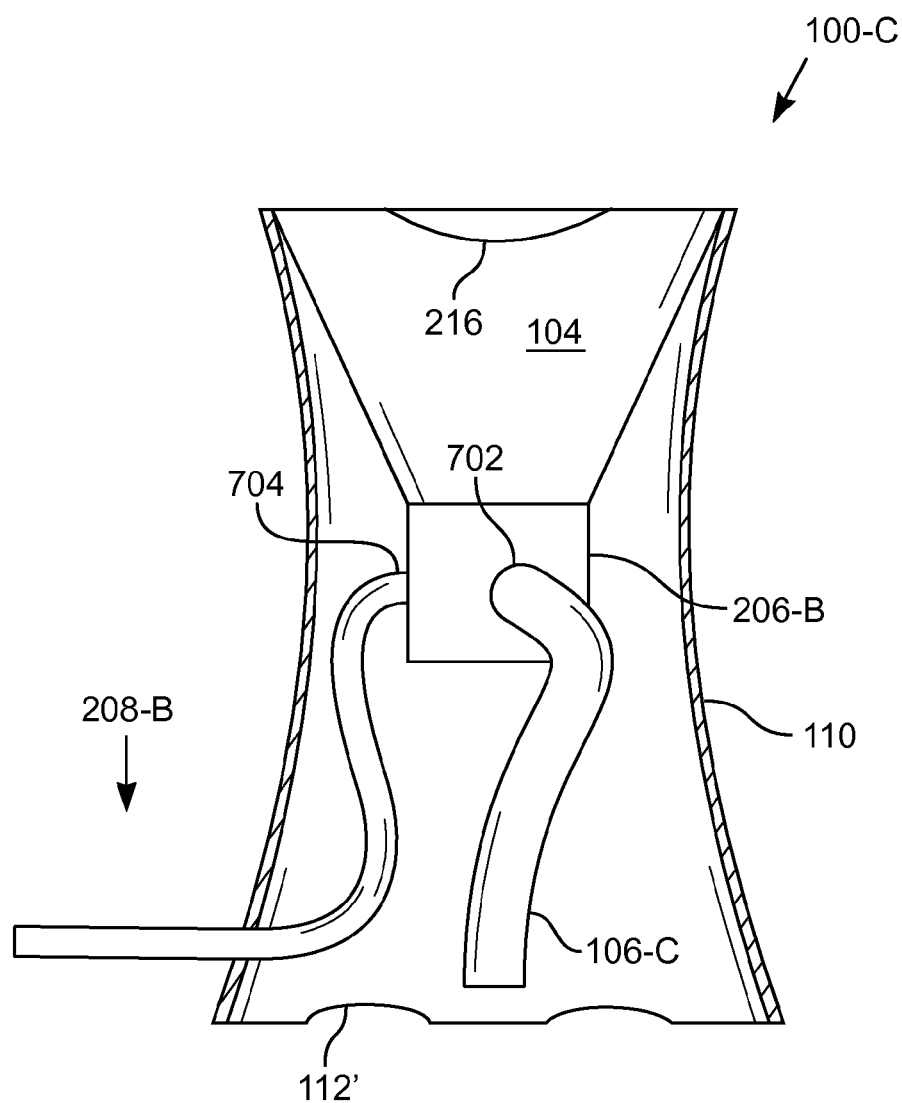
FIG. 7 is a partial cross-sectional view of still another embodiment of a waste receiving device.

FIG. 7 illustrates a partial cross-sectional view of still another embodiment of a waste receiving device 100-B. The shroud 110 is shown in cross-section with the top of the receiver 104 attached to the top of the shroud 110. The bottom of the receiver 104 is attached to a masticator 206-B. In the illustrated embodiment, the masticator 206-B has a power source 208-B that is hydraulic, that is, pressurized water is fed to a pressurized water inlet 704 on the masticator 206-B. The masticator 206-B receives intake from the receiver 104 and discharges the masticated waste from an outlet 702 that is connected to a conduit 106-C. The outlet of the conduit 106-C is positioned to be adjacent the drain 102 in the floor.

The illustrated housing 110 has a hyperbolic-type shape with passages 112' on the lower edge of the housing 110. In other embodiments the housing 110 has other configurations, for example cylindrical or polygonal. The passages 112' are sized to allow water on the floor outside the housing 110 to flow to the drain 102 inside the housing 110. The passages 112 allow the floor drain 102 under the waste receiving device 100 to be open, that is, the drain 102 does not have a cover or strainer. The housing 110 with passages 112 prevents undesired objects from entering the open drain 102 and the open drain 102 has a large opening for receiving fecal waste that, typically, would be stopped or slowed down by the drain strainer.

The hydraulically operated masticator 206-B uses a supply of pressurized water as the power source 208-B to drive the masticator 206-B. The pressurized water supply 208-B, in one embodiment, is part of the permanent plumbing and is plumbed to the masticator 206-B. In another embodiment, the pressurized water supply 208-B is a water hose that is connected to a fitting positioned on or inside the housing 110.

In another embodiment, the power source 208 is electrical. Electrical power is fed to the masticator 206, which is an electrically operated device for masticating the waste. In still another embodiment, the power source 208 is pneumatic and the a compressed gas is fed to the masticator 206.

The waste receiving device 100 includes various functions. The function of filtering the fecal waste 202 is implemented, in various embodiments, by a strainer 204, such as illustrated in FIGS. 2 to 4. The function of filtering, in one embodiment, includes a strainer 204 with a plurality of openings or apertures 304 that allow passage of fecal waste 202 that has a size and consistency that will pass through the drain 102.

The function of masticating the fecal waste 202 is implemented, in various embodiments, by the masticator 206 and an associated power source 208, such as illustrated in FIGS. 2 and 5 to 7. In one embodiment, the masticator 206-A is a mechanical device with a human operated power source 208-A, such as a foot pedal. In another embodiment, the masticator 206-B is a device that is connected to an electrical or hydraulic power supply 208-B that drives the masticator 206-B.

The function of allowing passage of environmental fluid 212 is implemented, in one embodiment, by the passages, or openings, 112 adjacent the bottom edge of the housing 110.

The function of supporting the receiver 104 is implemented, in one embodiment, by the housing 110. In other embodiments, the function of supporting the receiver 104 is implemented by a frame, such as legs or other support members, that holds the receiver 104 in a fixed relative position above a drain 102.

From the foregoing description, it will be recognized by those skilled in the art that a waste receiving device 100 has been provided. The waste receiving device 100, in one embodiment, includes a receiver 104 and a conduit 106. The receiver 104 receives waste as it is produced by an incontinent person being bathed. The receiver 104 has an orifice at its upper end. The receiver 104 communicates with the conduit 106 at its lower end. In various embodiments, the waste receiving device 100 includes a strainer 204 and/or a masticator 206 and power source 208. The strainer 204 includes apertures 304 that pass waste that will flow through a nearby drain 102. The masticator 206 processes the waste 202 such that the waste has a consistency that is suitable for passage through the drain 102.

The receiver 104 and the conduit 106 are surrounded by a shroud 110. The shroud 110 provides support to the receiver 104. The shroud 110, in one embodiment, is secured to the floor by mounts 114. The lower edge of the shroud 110 substantially matches the contour of the floor. When the receiving device 100 is installed into a shower room, the bottom of the shroud 110 includes grooves or passages 112 that pass water through the shroud 110 toward the drain 102.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. An apparatus for receiving fecal waste from a person, said apparatus comprising:
   a receiver having an opening configured to receive fecal waste from a person;
   a waste processing mechanism having an input in communication with said receiver, said waste processing mechanism having an outlet passing processed waste, said processed waste having a maximum solids size that is suitable for passing through a waste water drain that is not configured to receive raw human fecal waste;
   a conduit configured to discharge to said waste water drain, said conduit in communication with said outlet of said waste processing mechanism; and
   a shroud supporting said receiver, said shroud having a lower end extending further than a distal end of said conduit whereby said distal end of said conduit is supported above said waste water drain, said shroud enclosing said waste processing mechanism and said conduit, said lower end of said shroud having at least one passage dimensioned and configured to allow a liquid to flow from outside said shroud to inside said shroud whereby said liquid from outside said shroud is free to enter said waste water drain.

2. The apparatus of claim 1 wherein said waste processing mechanism includes a strainer having an aperture, said aperture having a size corresponding to said maximum solids size.

3. The apparatus of claim 1 wherein said waste processing mechanism includes a masticator configured to reduce said fecal waste to a consistency suitable for passing through said drain.

4. The apparatus of claim 3 wherein said masticator is a mechanical reducer operatively connected to a foot pedal.

5. The apparatus of claim 3 wherein said masticator is a mechanical reducer including a plurality of fingers attached to a rotatable shaft, said plurality of fingers engaging a plurality of slots whereby said fecal matter is masticated when said plurality of fingers engages said plurality of slots.

6. The apparatus of claim 3 wherein said masticator includes a pressurized water inlet, said masticator operable when a supply of pressurized water is available at said pressurized water inlet.

7. The apparatus of claim 3 wherein said masticator further includes a strainer positioned to filter said fecal matter before said masticator receives said fecal matter, said strainer having an aperture sized to prevent passage of fecal matter solids having a size greater than a specified maximum size.

8. The apparatus of claim 1 wherein said receiver includes a lip, said lip having a notch, said notch positioned on a side of said receiver that first encounters a commode apparatus when said receiver cooperates with said commode apparatus, said notch being dimensioned to provide clearance from any dangling body parts of an occupant of said commode apparatus when said commode apparatus is moved relative to said receiver.

9. The apparatus of claim 1 wherein said receiver is supported at a height cooperating with a commode apparatus such that said receiver is positioned to receive said fecal matter from an occupant of said commode apparatus.

10. An apparatus for receiving fecal waste from a person, said apparatus comprising:
    a receiver having an opening configured to receive fecal waste from a person;
    a strainer having an input in communication with said receiver, said strainer having an aperture, said aperture having a size corresponding to a maximum solids size, said strainer having an outlet passing processed waste, said maximum solids size suitable for passing through a waste water drain; and
    a conduit configured to discharge to said waste water drain, said conduit in communication with said outlet of said strainer; and
    a support structure supporting said conduit and said receiver, said support structure having a lower end configured to engage a floor, said lower end of said support structure extending beyond said distal end of said conduit, said support structure being dimensioned to support a distal end of said conduit above said waste water drain when said support structure is engaging said floor, wherein said support structure has at least one passage proximate said lower end, said at least one passage dimensioned and configured to allow a liquid to flow from outside said support structure and enter said waste water drain.

11. The apparatus of claim 10 wherein said strainer cooperates with a masticator configured to reduce said fecal waste to a consistency suitable for passing through said drain.

12. The apparatus of claim 11 wherein said masticator includes a pressurized water inlet, said masticator operable when a supply of pressurized water is available at said pressurized water inlet.

13. The apparatus of claim 10 wherein said receiver is supported at a height cooperating with a commode apparatus such that said receiver is positioned to receive said fecal matter from an occupant of said commode apparatus, said commode apparatus being a mobile device positionable over said receiver, said receiver having a lip with a depression extending from an outside to an inside of said receiver wherein said lip is lower proximate said depression than elsewhere, said depression dimensioned and positioned to provide clearance from any dangling body parts of an occupant of said commode apparatus when said commode apparatus is moved relative to said receiver.

14. An apparatus for receiving fecal waste from a person, said apparatus comprising:
    a receiver having an opening configured to receive fecal waste from a person;
    a masticator configured to receive said fecal waste from said receiver, said masticator configured to reduce said fecal waste to output processed waste, said processed waste having a maximum solids size that is suitable for passing through a waste water drain;
    a conduit configured to discharge said processed waste to said waste water drain; and
    a support structure supporting said receiver, said support structure having a lower end extending further than a distal end of said conduit whereby said distal end of said conduit is supported above said waste water drain, said support structure enclosing said waste processing mechanism and said conduit, said lower end of said support structure having at least one passage allowing a liquid to flow from outside said support structure to inside of said support structure whereby said liquid from outside said support structure is free to enter said waste water drain.

15. The apparatus of claim 14 wherein said masticator is a mechanical reducer including a plurality of fingers attached to a rotatable shaft, said plurality of fingers engaging a plurality of slots whereby said fecal matter is masticated when said plurality of fingers engages said plurality of slots.

16. The apparatus of claim 14 wherein said masticator includes a pressurized water inlet, said masticator operable when a supply of pressurized water is available at said pressurized water inlet.

17. The apparatus of claim 14 wherein said masticator further includes a strainer positioned to filter said fecal matter before said masticator receives said fecal matter, said strainer having an aperture sized to prevent passage of fecal matter solids having a size greater than a specified maximum size.

18. The apparatus of claim 14 wherein said receiver is supported at a height cooperating with a commode apparatus such that said receiver is positioned to receive said fecal matter from an occupant of said commode apparatus.

19. The apparatus of claim 14 wherein said receiver includes a lip, said lip having a notch extending from an outside to an inside of said receiver wherein said lip is lower proximate said notch than elsewhere, said notch positioned on a side of said receiver configured to first encounter a commode apparatus when said receiver cooperates with said commode apparatus, said notch being dimensioned to provide clearance from any dangling body parts of an occupant of said commode apparatus when said commode apparatus is moved relative to said receiver.

* * * * *